United States Patent
Gong et al.

(10) Patent No.: US 7,915,405 B2
(45) Date of Patent: Mar. 29, 2011

(54) 2,4-DISUBSTITUTED-5-AMINOCARBONYL-1,3-THIAZOLE DERIVATIVES FOR THERAPEUTIC AGENT OF ANTIINFLAMMATORY DISEASE, METHOD THEREOF FOR PREPARATION, THERAPEUTIC AGENT FOR ANTIINFLAMMATORY DISEASE INDUCED BY SPC ACTIVITY CONTAINING THE SAME

(75) Inventors: Young-Dae Gong, Daejeon (KR); Taeho Lee, Daejeon (KR); Moon-Kook Jeon, Daejeon (KR); Heeyeong Cho, Daejun (KR); Jae Yang Kong, Seoul (KR); Gildon Choi, Daejun (KR); Dae Young Jeong, Daejeon (KR); Soon-Hee Hwang, Daejun (KR)

(73) Assignee: Korea Research Institute of Chemical Technology, Daejun (KR)

( * ) Notice: Subject to any disclaimer, the term of this patent is extended or adjusted under 35 U.S.C. 154(b) by 0 days.

(21) Appl. No.: 12/570,492

(22) Filed: Sep. 30, 2009

(65) Prior Publication Data

US 2010/0145043 A1  Jun. 10, 2010

(30) Foreign Application Priority Data

Dec. 5, 2008  (KR) .................. 10-2008-0123619

(51) Int. Cl.
| | | |
|---|---|---|
| C07D 413/14 | (2006.01) | |
| C07D 413/10 | (2006.01) | |
| C07D 417/10 | (2006.01) | |
| C07D 417/14 | (2006.01) | |
| C07D 277/54 | (2006.01) | |
| A61K 31/5377 | (2006.01) | |
| A61K 31/497 | (2006.01) | |
| A61K 31/454 | (2006.01) | |
| A61K 31/431 | (2006.01) | |

(52) U.S. Cl. .......... 544/82; 544/121; 544/129; 544/133; 546/209; 546/270.7; 548/192; 514/232.2; 514/235.8; 514/236.8; 514/253.09; 514/254.04; 514/326; 514/369

(58) Field of Classification Search .................. None
See application file for complete search history.

(56) References Cited

FOREIGN PATENT DOCUMENTS

| KR | 1020090032372 A | 1/2009 |
|---|---|---|
| WO | WO/2006/019451 A1 | 5/2006 |

OTHER PUBLICATIONS

Kazuhiko Higuchi et al., The skin of atopic dermatitis . . . , publication, 2000, 10 pages, pp. 747-756, Biochem. J. (2000) 350, 747-756 (Printed in Great Britain).

Naishadh N. Desai et al., Sphingosylphosphorylcholine is a remarkable potent . . . , publication, Nov. 27, 1991, 6 pages, pp. 361-366, vol. 181, No. 1, 1991 Biochemical and Biophysical Research Communications.

George Boguslawski et al., Sphingosylphosphorylcholine Induces Endothelial, publication, 2000, 7 pages, pp. 603-609, Biochemical and Biophysical Research Communication 272, 603-609 (2000).

Eun Su Jeon et al., Role of MEK-ERK pathway in . . . , publication, 2005, 9 pages, pp. 25-33, Biochimica et Biophysica Acta 1734 (2005) 25-33.

Reiko Okamoto et al., Sphingosylphosphorylcholine is upregulated in the stratum . . . , publication, 2003, 10 pages, pp. 93-102, Journal of Lipid research vol. 44, 2003.

Junko Hara et al., High-Expression of Sphingomyelin . . . , publication, 2000, 8 pages, pp. 406-413, The Society for Investigative Dermatology, Inc.

Kazuhiko Higuchi et al., Sphingosylphosphorylcholine is an activator . . . , publication, 2001, 9 pages, pp. 1562-1570, Journal of Lipid Research vol. 42, 2001.

Terumasa Hashimoto et al.., Itch-Scrath Responses Induced . . . , publication, 2004, 7 pages, Pharmacology 2004; 72:51-56.

Ian L.P. Beales, Gastrin and interleukin-1β stimulate . . . , publication, 2004, 12 pages, pp. 2983-2995, Life Sciences 75 (2004) 2983-2995.

L. M. De Young et al., Edema and cell infiltration in the phorbol . . . , publication, 1989, 7 pages, pp. 335-341, Agents and Actions, vol. 26, 3/4 (1989).

*Primary Examiner* — Kamal A Saeed
*Assistant Examiner* — Nyeemah Grazier
(74) *Attorney, Agent, or Firm* — Reinhart Boerner Van Deuren P.C.

(57) ABSTRACT

Disclosed herein are 2,4-disubstituted-5-aminocarbonyl-1,3-thiazole derivatives, a preparation method thereof, and a therapeutic agent for treating inflammatory diseases induced by SPC, which contains the derivative as an active ingredient. The anti-inflammatory effect of the 2,4-disubstituted-5-aminocarbonyl-1,3-thiazole derivatives was analyzed through a test employing human dermal cells and an animal test using mice and, as a result, it was found that the derivatives showed excellent inhibitory activity on SPC receptor compared to thiazole derivatives known in the prior art. Thus, the 2,4-disubstituted-5-aminocarbonyl-1,3-thiazole derivatives or pharmaceutically acceptable salts thereof are useful as active ingredients in therapeutic agents for treating inflammatory diseases, such as inflammation, pruritus and skin infection, which appear in atopic dermatitis and other diseases induced by SPC activity.

[Formula 1]

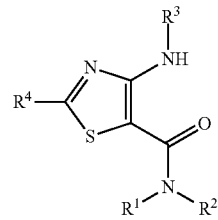

wherein $R^1$, $R^2$, $R^3$ and $R^4$ are as defined in the specification.

7 Claims, No Drawings

2,4-DISUBSTITUTED-5-AMINOCARBONYL-1,3-THIAZOLE DERIVATIVES FOR THERAPEUTIC AGENT OF ANTIINFLAMMATORY DISEASE, METHOD THEREOF FOR PREPARATION, THERAPEUTIC AGENT FOR ANTIINFLAMMATORY DISEASE INDUCED BY SPC ACTIVITY CONTAINING THE SAME

CROSS-REFERENCE TO RELATED PATENT APPLICATIONS

This patent application claims the benefit of co-pending Korean Patent Application No. 2008-123619, filed Dec. 5, 2008, the entire teachings and disclosure of which are incorporated herein by reference thereto.

BACKGROUND OF THE INVENTION

1. Field of the Invention

The present invention relates to 2,4-disubstituted-5-aminocarbonyl-1,3-thiazole derivatives for treating inflammatory diseases, a preparation method thereof, and a therapeutic agent for treating inflammatory diseases induced by SPC activity, which contains the derivatives as an active ingredient, and more particularly to 2,4-disubstituted-5-aminocarbonyl-1,3-thiazole derivatives, which are novel compounds showing SPC inhibitory activity, a preparation method thereof, and a therapeutic agent for treating inflammatory diseases induced by SPC activity, which contains the derivatives as an active ingredient.

2. Description of the Prior Art

Sphingosylphosphorylcholine (hereinafter referred to as "SPC"), together with sphingosine-1-phosphate (S1P) and lysophosphatidic acid (LPA) structurally similar thereto, is a member of the lysophospholipid class of phospholipids. These substances act as important signaling mediators in immune functions, such as cellular proliferation and migration, and inflammatory reactions.

SPC is produced from sphingomyelin (a component of the cell membrane) by sphingomyelin deacylase [Higuchi K, *Biochem J.*, 2000, 350, 747-56]. Also, SPC is known to be deeply involved in the growth and proliferation of various cells [Desai, *Biochem. Biophys. Res. Commun.*, 1991, 181, 361-366], angiogenesis [Boguslawski, *Biochem. Biophys. Res. Commun.*, 2000, 272, 603-609], and apoptosis [Jeon E S, *Biochim Biophys Acta.*, 2005, 1734(1); 25-33].

A typical example of SPC-related disease is atopic dermatitis. In atopic dermatitis, due to a decrease in the lipid content of the horny layer, antimicrobial activity is reduced and the skin's horny layer is weakened, and thus a defense against external stimuli is reduced, whereby inflammatory reactions occur, leading to itching. Moreover, itching causes secondary infection, thus causing hyper-immune responses.

Particularly, it is known that, in normal persons, SPC is not substantially present or is detected at very low concentrations, but it is increased several thousand times in the dermatitis of atopic dermatitis patients [Higuchi K, *Biochem. J.*, 2000, 350, 747-756; Reiko Okamoto, *Journal of Lipid Research*, 2003, 44, 93-102]. The chief cause is the deficiency of ceramide in the horny layer of atopic dermatitis patients [Junko Hara, *J. invest. Dermatol.*, 2000, 115, 406-413]. Also, SPC plays an important role in the altered keratinization process of epidermis in atopic diseases [Higuchi, *J. Lipid Res.*, 2001, 42, 1562-1570]. Such study results suggest that SPC is the direct cause of skin barrier disruption, a typical symptom of atopic disease, and can cause secondary inflammatory reactions. Accordingly, a substance of controlling the production of SPC can be used as a therapeutic agent for treating skin inflammatory diseases.

Meanwhile, with respect to itching which causes the patient's pain and decreases the patient's life quality, among symptoms of atopic dermatitis, it was reported that lysophosphatidic acid (LPA) structurally similar to SPC causes itching [Hashimoto, *Pharmacology*, 2004, 72, 51-56]. Thus, it can be inferred that SPC can also cause itching in the body. In addition, it was recently demonstrated that intradermal injection of SPC can directly cause itching [International patent Publication Ser. No. 06/049,451].

The present inventors previously developed novel thiazole derivatives for treating inflammatory diseases induced by SPC activity [Korean. Patent Application No. 2007-97553].

Accordingly, the present inventors have screened novel compounds, which can be used as therapeutic agents for treating inflammatory diseases having improved efficiency, from N-{5-benzoyl-2-[4-(2-methoxyphenyl)piperazin-1-yl] thiazol-4-yl}pivalamide compounds among the above-mentioned thiazole derivatives. As a result, the present inventors have prepared 2,4-disubstituted-5-aminocarbonyl-1,3-thiazole derivative compounds through an improved solid-phase synthetic process, have examined the anti-inflammatory effects of the 2,4-disubstituted-5-aminocarbonyl-1,3-thiazole derivative compounds through a test employing human dermal cells and an animal test employing mice and, as a result, have found that the derivative compounds have excellent inflammation inhibitory effects, thereby completing the present invention.

SUMMARY OF THE INVENTION

It is an object of the present invention to provide 2,4-disubstituted-5-aminocarbonyl-1,3-thiazole derivatives prepared using a combinatorial chemical synthetic technique.

Another object of the present invention is to provide a therapeutic agent for treating inflammatory diseases induced by SPC activity, which contains a 2,4-disubstituted-5-aminocarbonyl-1,3-thiazole derivative as an active ingredient.

To achieve the above objects, the present invention provides 2,4-disubstituted-5-aminocarbonyl-1,3-thiazole derivatives represented by the following formula 1:

[Formula 1]

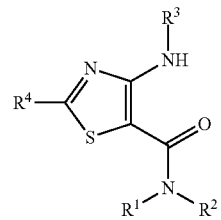

wherein $R^1$ and $R^2$ are the same or different and are each a $C_1$-$C_{10}$ linear, branched or cyclic alkyl group, or a cyclic $C_1$-$C_{10}$ alkyl group containing a heteroatom (—NH—, —S— or —O—) or heteroalkyl group, $R^3$ is a carbonyl group containing at least one of a $C_1$-$C_{10}$ linear, branched or cyclic alkyl group, a $C_1$-$C_{10}$ alkoxy group, a $C_2$-$C_{10}$ alkenyl group, a $C_2$-$C_{10}$ alkynyl group, a heteroaryl group, an arylalkyl group, a $C_5$-$C_{10}$ heteroarylalkyl group, a phenyl or a substituted phenyl group, and $R^4$ is an amino group substituted with one or more of a $C_1$-$C_{10}$ linear, branched or cyclic alkyl group, a $C_1$-$C_{10}$ aryl group, a $C_1$-$C_{10}$ heteroaryl group, a $C_1$-$C_{10}$ arylalkyl group or $C_1$-$C_{10}$ heteroarylalkyl group, or an amine containing a piperazine substituted with a $C_1$-$C_{10}$ linear, branched or cyclic alkyl group, a phenyl or a substituted phenyl or a heteroarylamide group, wherein the substituted phenyl group in $R^3$ and $R^4$ represents a phenyl group substituted with 1 to 4 substituents selected from the group consisting of a halogen atom, a nitro group, a $C_1$-$C_{10}$ alkyl group, a $C_1$-$C_{10}$ alkoxy group and a $C_1$-$C_{10}$ haloalkyl group.

Preferably, $R^1$ and $R^2$ in the 2,4-disubstituted-5-aminocarbonyl-1,3-thiazole derivatives are the same or different and are each selected from the group consisting of a $C_1$-$C_5$ linear or branched alkyl group, a $C_5$-$C_7$ cyclic alkyl group, and a $C_5$-$C_7$ cyclic alkyl group containing a heteroatom (—NH—, —S— or —O—) or a heteroalkyl group, $R^3$ is a carbonyl group containing at least one of a $C_1$-$C_5$ linear, branched or cyclic alkyl group, a $C_2$-$C_5$ alkenyl group, a $C_2$-$C_5$ alkynyl group, a heteroaryl group, an arylalkyl group, a $C_5$-$C_{10}$ heteroarylalkyl group, a phenyl or a substituted phenyl group, and $R^4$ is an amino group substituted with one or more of a $C_2$-$C_7$ linear, branched or cyclic alkyl group, a $C_1$-$C_5$ aryl group, a $C_1$-$C_5$ heteroaryl group, a $C_1$-$C_5$ arylalkyl group or a $C_1$-$C_5$ heteroarylalkyl group, or an amine containing a piperazine substituted with a $C_1$-$C_7$ linear, branched or cyclic alkyl group, a phenyl or substituted phenyl group or a heteroarylamide group, wherein the substituted phenyl group in $R^3$ and $R^4$ is a phenyl group substituted 1 to 4 substituents selected from the group consisting of a halogen atom, a nitro group, a $C_1$-$C_5$ alkyl group, a $C_1$-$C_5$ alkoxy group and a $C_1$-$C_5$ haloalkyl group.

The present invention provides a method of preparing 2,4-disubstituted-5-aminocarbonyl-1,3-thiazole derivatives represented by formula 1 using a combinatorial chemical synthetic technique.

The present invention also provides a composition for treating inflammatory diseases induced by SPC activity, which contains a 2,4-disubstituted-5-aminocarbonyl-1,3-thiazole derivative represented by formula 1 or a pharmaceutically acceptable salt thereof as an active ingredient. Namely, the 2,4-disubstituted-5-aminocarbonyl-1,3-thiazole derivatives represented by formula 1 or pharmaceutically acceptable salts thereof are useful as therapeutic agents for treating inflammatory diseases induced by SPC activity.

Furthermore, the inventive 2,4-disubstituted-5-aminocarbonyl-1,3-thiazole derivatives represented by formula 1 or pharmaceutically acceptable salts thereof are useful as skin external agents for inhibiting post-traumatic scar formation and promoting wound healing.

In addition, the present invention provides an angiogenesis inhibitor for inhibiting angiogenesis in tumors by inhibiting cell chemotactic migration caused by SPC, the angiogenesis inhibitor containing a 2,4-disubstituted-5-aminocarbonyl-1, 3-thiazole derivative represented by formula 1 or a pharmaceutically acceptable salt thereof as an active ingredient.

The present invention provides 2,4-disubstituted-5-aminocarbonyl-1,3-thiazole derivatives or pharmaceutically acceptable salts thereof, which are prepared using a combinatorial chemical synthetic technique. The anti-inflammatory effects of the derivatives were analyzed through a test employing human dermal cells and an animal test employing mice and, as a result, it was found that the derivatives showed excellent inhibitory activity on SPC receptor. Thus, the 2,4-disubstituted-5-aminocarbonyl-1,3-thiazole derivatives or pharmaceutically acceptable salts thereof are useful for treating inflammatory diseases induced by SPC activity.

DETAILED DESCRIPTION OF THE INVENTION

Hereinafter, the present invention will be described in detail.

The present invention provides 2,4-disubstituted-5-aminocarbonyl-1,3-thiazole derivatives represented by the following formula 1:

[Formula 1]

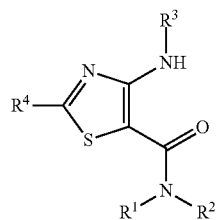

wherein $R^1$ and $R^2$ are the same or different and are each a $C_1$-$C_{10}$ linear, branched or cyclic alkyl group, or a cyclic $C_1$-$C_{10}$ alkyl group containing a heteroatom (—NH—, —S— or —O—) or heteroalkyl group, $R^3$ is a carbonyl group containing at least one of a $C_1$-$C_{10}$ linear, branched or cyclic alkyl group, a $C_1$-$C_{10}$ alkoxy group, a $C_2$-$C_{10}$ alkenyl group, a $C_2$-$C_{10}$ alkynyl group, a heteroaryl group, an arylalkyl group, a $C_5$-$C_{10}$ heteroarylalkyl group, a phenyl or a substituted phenyl group, and $R^4$ is an amino group substituted with one or more of a $C_1$-$C_{10}$ linear, branched or cyclic alkyl group, a $C_1$-$C_{10}$ aryl group, a $C_1$-$C_{10}$ heteroaryl group, a $C_1$-$C_{10}$ arylalkyl group or $C_1$-$C_{10}$ heteroarylalkyl group, or an amine containing a piperazine substituted with a $C_1$-$C_{10}$ linear, branched or cyclic alkyl group, a phenyl or a substituted phenyl or a heteroarylamide group, wherein the substituted phenyl group in $R^3$ and $R^4$ represents a phenyl group substituted with 1 to 4 substituents selected from the group consisting of a halogen atom, a nitro group, a $C_1$-$C_{10}$ alkyl group, a $C_1$-$C_{10}$ alkoxy group and a $C_1$-$C_{10}$ haloalkyl group.

Preferably, $R^1$ and $R^2$ in the 2,4-disubstituted-5-aminocarbonyl-1,3-thiazole derivatives are the same or different and are each selected from the group consisting of a $C_1$-$C_5$ linear or branched alkyl group, a $C_5$-$C_7$ cyclic alkyl group, and a $C_5$-$C_7$ cyclic alkyl group containing a heteroatom (—NH—, —S— or —O—) or a heteroalkyl group, $R^3$ is a carbonyl group at least one of a $C_1$-$C_5$ linear, branched or cyclic alkyl group, a $C_2$-$C_5$ alkenyl group, a $C_2$-$C_5$ alkynyl group, a heteroaryl group, an arylalkyl group, a $C_5$-$C_{10}$ heteroarylalkyl group, a phenyl or a substituted phenyl group, and $R^4$ is an amino group substituted with one or more of a $C_2$-$C_7$ linear, branched or cyclic alkyl group, a $C_1$-$C_5$ aryl group, a $C_1$-$C_5$ heteroaryl group, a $C_1$-$C_5$ arylalkyl group or a $C_1$-$C_5$ heteroarylalkyl group, or an amine containing a piperazine substituted with a $C_1$-$C_7$ linear, branched or cyclic alkyl group, a phenyl or substituted phenyl group or a heteroarylamide group, wherein the substituted phenyl group in $R^3$ and $R^4$ is a phenyl group substituted 1 to 4 substituents selected from the group consisting of a halogen atom, a nitro group, a $C_1$-$C_5$ alkyl group, a $C_1$-$C_5$ alkoxy group and a $C_1$-$C_5$ haloalkyl group.

Furthermore, the present invention may provide pharmaceutically acceptable salts of the 2,4-disubstituted-5-aminocarbonyl-1,3-thiazole derivatives represented by formula 1. The pharmaceutically acceptable salt in the present invention can be prepared according to any conventional method known in the art, for example, by allowing the compound of the present invention with an inorganic acid such as hydrochloric acid, hydrobromide, sulfuric acid, sodium hydrogen sulfate, phosphoric acid or carbonic acid; an organic acid such as formic acid, acetic acid, oxalic acid, benzoic acid, citric acid, tartaric acid, gluconic acid, gentisic acid, fumaric acid, lactobionic acid, salicylic acid, or acetylsalicylic acid (aspirin); an alkali metal ion such as sodium or potassium; or ammonium ion.

The inventive 2,4-disubstituted-5-aminocarbonyl-1,3-thiazole derivatives represented by formula 1 are prepared according to the following reaction scheme through a combinatorial chemical synthetic technique using a solid-phase parallel synthetic method:

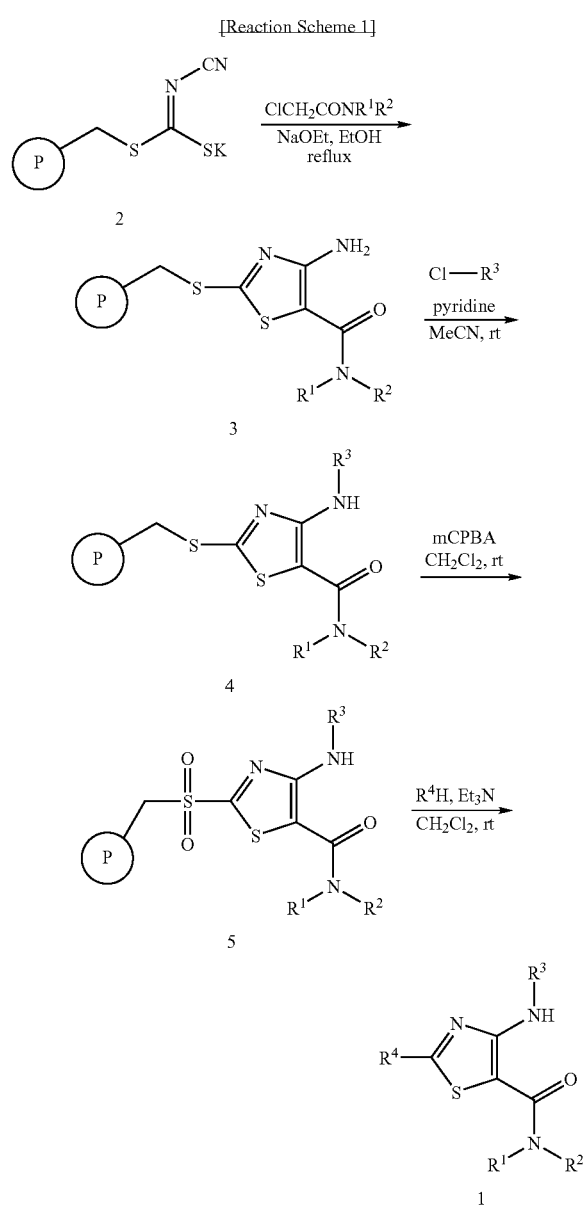

wherein R', $R^2$, $R^3$ and $R^4$ are as defined in the specification, and Ⓟ represents a solid support in the form of a polymer selected from the group consisting of polystyrene-divinylbenzene, metacrylic acid-dimethylacrylamide, and hydroxyl methacrylic acid.

Specifically, the preparation method of the present invention comprises the steps of:

(1) allowing a thioiminocarbonate containing a sulfanyl linker, represented by formula 2 in reaction scheme 1, to react with a 2-chloroacetoamide derivative, thus synthesizing a 4-amino-5-aminocarbonyl-1,3-thiazolesulfanyl resin introduced with $R^1$ and $R^2$, represented by formula 3 in reaction scheme 1;

(2) polymerizing the 4-amino group of the compound of formula 3 with carboxylic acid chloride, thus synthesizing a 4-N-acyl-5-aminocarbonyl-1,3-thiazolesulfanyl resin introduced with $R^3$, represented by formula 4;

(3) oxidizing the sulfanyl linker resin moiety of the compound of formula 4, thus synthesizing a 4-N-acyl-5-aminocarbonyl-1,3-thiazolesulfanyl resin containing a sulfanyl linker resin, represented by formula 5 in reaction scheme 1; and (4) subjecting the compound of formula 5 to elimination and addition reactions with primary or secondary amine, thus synthesizing a 2,4-disubstituted-5-aminocarbonyl-1,3-thiazole derivative represented by formula 1.

Hereinafter, the reaction process, the solvent system composition and the reaction conditions, which are used in the present invention, will be described in detail.

In the present invention, an organic solvent showing an excellent swelling effect on Wang resin or Merrifield resin is used as a solvent.

In step (1), dimethylformamide (DMF), acetone, methanol or ethanol is used as a solvent. Preferably, ethanol is used. In the reaction of step (1), each of an acetoamide substitute introduced with $R^1$ and $R^2$ and a base is preferably used in an amount of about 3 equivalents, and more preferably about 2 equivalents in view of cost-effectiveness. As the base, N,N-diisopropylethylamine, triethylamine ($Et_3N$), sodium methoxide (NaOMe) or sodium ethoxide (NaOEt) may typically be used. Preferably, sodium ethoxide is used. Also, as the $R^1$ and $R^2$ substituents, alkyl halides as defined above may be used.

In step 2, acetonitrile (MeCN) or dichloromethane ($CH_2Cl_2$) is used as a solvent. In the reaction of step (2), each of a base and an $R^3$ substituent is preferably in an amount of about 3 equivalents, and more preferably about 2 equivalents in view of cost-effectiveness. As the base, pyridine, triethylamine or the like may typically be used. As the $R^3$ substituent, carboxylic acid chloride as defined above may be used.

In step (3), dichloromethane is used as a solvent. In the reaction of step (3), meta-chloroperbenzoic acid or hydrogen peroxide is preferably used in an amount of about 4 equivalents, and more preferably about 2.5 equivalents in view of cost-effectiveness.

In step (4), elimination and addition reactions are performed using a dioxane or dichloromethane solution, a $R^4$ substituent and a base, thus obtaining the inventive 2,4-disubstituted-5-aminocarbonyl-1,3-thiazole derivative represented by formula 1. In the reaction of step (4), each of the base and the $R^4$ substituent is preferably used in an amount of about 2.5 equivalents, and more preferably about 1.5 equivalents in view of cost-effectiveness. As the base, pyridine, triethylamine or the like may typically be used, and as the $R^4$ substituent, primary or secondary amine as defined above may be used.

In order to confirm the synthesis of the 2,4-disubstituted-5-aminocarbonyl-1,3-thiazole derivatives, the target compound isolated from the compound of formula 5 may be purified by column chromatography in the final step, and its structure is analyzed with NMR and/or Mass spectroscopy.

The progress of reaction may be monitored with ATR-FTIR for detecting the intermediates, the resins of formulae 3, 4 and 5.

The present invention provides a therapeutic agent for treating inflammatory diseases induced by SPC activity, which contains the 2,4-disubstituted-5-aminocarbonyl-1,3-thiazole derivative represented by formula 1 or a pharmaceutically acceptable salt thereof as an active ingredient.

The 2,4-disubstituted-5-aminocarbonyl-1,3-thiazole derivatives of the present invention were tested on an effect on cellular division and proliferation and, as a result, it was found that the compounds of the present invention had an antagonistic effect on selective cell proliferation induced by SPC (see Table 2). Accordingly, the compounds of the present invention are effective for treating skin diseases such as atopic dermatitis, which are induced by excessive cellular division and proliferation caused by SPC.

Also, excessive cellular division and proliferation leads to scar formation due to an inflammatory reaction in the process in which an external wound is healed. However, the 2,4-disubstituted-5-aminocarbonyl-1,3-thiazole derivatives of the present invention inhibit cellular division and proliferation, and thus can be used as skin external agents for preventing unnecessary scar formation. In addition, the compounds of the present invention can be used to promote post-traumatic wound healing.

The 2,4-disubstituted-5-aminocarbonyl-1,3-thiazole derivative compounds of the present invention were tested for an inflammatory reaction induced by TPA and, as a result, it was found that the compounds of the present invention inhibited all ear edema and MPO activity and showed effects equal to those of hydrocortisone which is widely used as an anti-inflammatory drug (see Table 4).

Accordingly, the inventive 2,4-disubstituted-5-aminocarbonyl-1,3-thiazole derivatives or pharmaceutically acceptable salts thereof are effective for treating inflammation, pruritus, skin infection, etc., which appear in atopic dermatitis and other diseases. In addition, the compounds of the present invention are useful as skin external agents for inhibiting post-traumatic scar formation and promoting wound healing.

Preferred examples of the 2,4-disubstituted-5-aminocarbonyl-1,3-thiazole derivatives include N-{5-(morpholine-4-carbonyl)-2-[2-(piperidin-1-yl)ethylamino]thiazol-4-yl}pivalamide (Example 1-12), N-[2-(benzylamino)-5-(piperidine-1-carbonyl)thiazol-4-yl]pivalamide (Example 1-29) and N-{2-[4-(2-methoxyphenyl)-piperazin-1-yl]-5-(piperidine-1-carbonyl)thiazol-4-yl}pivalamide (Example 1-31). If a therapeutic agent contains, as an active ingredient, any one selected from the group consisting of the preferred examples, it will be useful as a therapeutic agent for treating inflammatory diseases induced by SPC activity.

Furthermore, the present invention provides the use of the inventive 2,4-disubstituted-5-aminocarbonyl-1,3-thiazole derivatives represented by formula 1 or pharmaceutically acceptable salts thereof as agents for controlling cell chemotactic migration-mediated symptoms. The term "cell chemotactic migration" refers to a phenomenon in which endothelial cells or immune cells migrate by special cytokines or kemokines in a living body. In chemotactic migration, immune cells migrate to sites of inflammation, or angiogenesis occurs by endothelial cell migration.

Accordingly, the inventive 2,4-disubstituted-5-aminocarbonyl-1,3-thiazole derivatives represented by formula 1 were measured for cell chemotactic migration induced by SPC and, as a result, it was found that the compounds of the present invention strongly inhibited the migration of endothelial cells or immune cells in the living body (see Table 3).

Thus, an agent for controlling cell chemotactic migration-mediated symptoms, which contains the inventive 2,4-disubstituted-5-aminocarbonyl-1,3-thiazole derivative represented by formula 1 as an active ingredient, inhibits angiogenesis caused by endothelial cell migration and can control the amplification of immune responses to external antigens.

Specific examples of the cell chemotactic migration-mediated symptoms described above in the agent for controlling cell chemotactic migration-mediated symptoms are inflammation, pruritus and skin infection, which appear in atopic dermatitis and other diseases.

Accordingly, the present invention provides an angiogenesis inhibitor for inhibiting angiogenesis in tumors by inhibiting cell chemotactic migration induced by SPC, the angiogenesis inhibitor containing a 2,4-disubstituted-5-aminocarbonyl-1,3-thiazole derivative represented by formula 1 or a pharmaceutically acceptable salt thereof as an active ingredient.

Particularly, the angiogenesis inhibitor for inhibiting angiogenesis in tumors by inhibiting cell chemotactic migration induced by SPC contains N-{2-[4-(2-methoxyphenyl)-piperazin-1-yl]-5-(piperidine-1-carbonyl) thiazol-4-yl}pivalamide (Example 1-31) among the 2,4-disubstituted-5-aminocarbonyl-1,3-thiazole derivatives represented by formula 1, as an active ingredient.

Furthermore, the pharmaceutical composition of the present invention may further comprise a conventional nontoxic, pharmaceutically acceptable carrier, adjuvant and excipient in addition to the 2,4-disubstituted-5-aminocarbonyl-1,3-thiazole derivative represented by formula 1 or a pharmaceutically acceptable salt thereof, and be formulated into conventional formulations known in the pharmaceutical field, for example, formulations for oral administration such as tablets, capsules, troches, liquids or emulsions, or formulations for parental administration.

The preferred dosage of the inventive compound to be administered to the human body can vary depending on the age, sex and body weight of the individual patient, the mode of administration, and the patient's physical condition and disease severity, and is 0.01-1000 mg/day with reference to the application to an adult patient with a body weight of 70 kg. The compound of the present invention may be administered at regular time intervals according to the instruction of a physician ranging from one to several times per day.

Hereinafter, the present invention will be described in detail with reference to examples. It is to be understood, however, that these examples are illustrative purposes only and are not to be construed as limiting the scope of the present invention.

Example 1-1

Synthesis of 2,4-disubstituted-5-aminocarbonyl-1,3-thiazole derivative (formula 1-1)

Step 1: Substitution of potassium cyanocarboimidodithionate resin (formula 2) with 4-amino-5-aminocarbonyl-1,3-thiazole

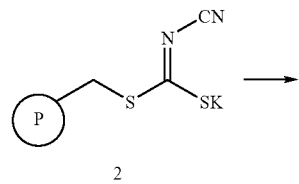

2

2.00 g (1.82 mmol) of a resin in the form of cyanocarboimidodithionate formula 2 was added to 20 in of ethanol and stirred at room temperature for 10 minutes. Then, 589 mg (3.60 mmol) of 2-chloro-1-morpholinoethanone and 277 mg (4.06 mmol) of sodium ethoxide (NaOEt) were added thereto, and the mixture was allowed to react by stirring at 80° C. for 12 hours. After completion of the reaction, the reaction mixture was filtered, and washed repeatedly with $H_2O$, DMF, MeOH and DCM, thus obtaining a 4-amino-5-aminocarbonyl-1,3-thiazole resin represented by formula 3-1 as a yellow solid.

Step 2: N-pivaloylation of 4-amino-5-aminocarbonyl-1,3-thiazole resin (formula 3-1)

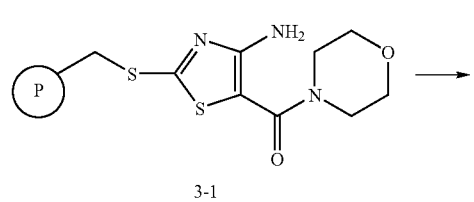

3-1

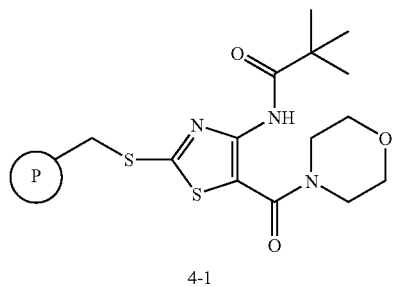

4-1

1.00 g (0.90 mmol) of the 4-amino-5-aminocarbonyl-1,3-thiazole resin represented by formula 3-1 was added to 10 ml of acetonitrile (MeCN) and stirred for 10 minutes, and then 0.94 ml (7.59 mmol) of pivaloyl chloride $(CH_3)_3CCOCl$) and 0.62 ml (7.50 mmol) of pyridine were added thereto. Then, the mixture was allowed to react by stirring at room temperature for 6 hours. After completion of the reaction, the reaction mixture was filtered, and washed repeatedly with $H_2O$, DMF, MeOH and DCM, thus obtaining a 4-N-pivaloyl-5-aminocarbonyl-1,3-thiazole resin represented by formula 4-1 as a brown solid.

Step 3: Oxidation of 4-N-pivaloyl-5-aminocarbonyl-1,3-thiazole resin (formula 4-1)

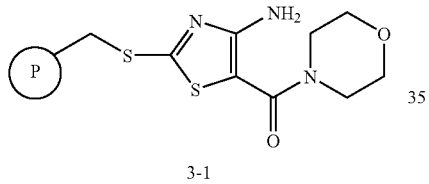

4-1

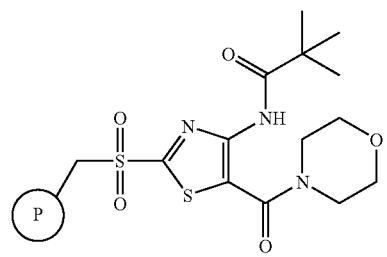

5-1

1.00 g (0.89 mmol) of the 4-N-pivaloyl-5-aminocarbonyl-1,3-thiazole resin containing a sulfanyl linker, represented by formula 4-1, was added to 10 ml of dichloromethane solution and stirred for 10 minutes. Then, 500 mg (2.23 mmol) of meta-chlorobenzoic acid (m-CPBA) was added thereto at room temperature, and then the mixture was allowed to react by stirring at room temperature for 12 hours. After completion of the reaction, the reaction mixture was filtered, and washed repeatedly with DMF, MeOH and DCM, thus obtaining a 4-N-pivaloyl-5-aminocarbonyl-1,3-thiazolesulfanyl resin represented by formula 5-1 as a yellow solid.

Step 4: Amination and elimination reactions of 4-N-pivaloyl-5-aminocarbonyl-1,3-thiazolesolfonyl resin (formula 5-1)

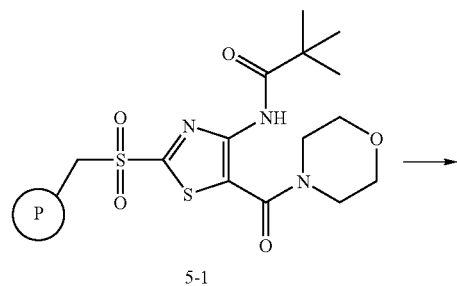

5-1

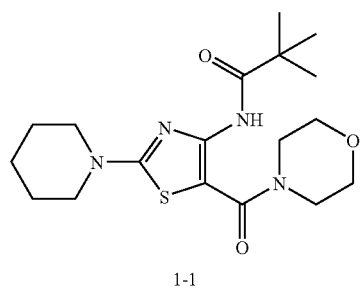

1-1

200 mg (0.17 mmol) of the 4-N-pivaloyl-5-aminocarbonyl-1,3-thiazole sulfanyl resin represented by formula 5-1 was added to 5 ml of dioxane solution and stirred at room temperature for 10 minutes. Then, 64 mg (0.31 mmol) of piperidine and 0.056 ml (0.40 mmol) of triethylamine were added thereto and allowed to react by stirring at room temperature for 12 hours. After completion of the reaction, the reaction mixture was filtered, and the filtrate was washed repeatedly with dichloromethane and methyl alcohol, and then concentrated under reduced pressure. The concentrate was separated and purified using a mixed solvent of hexane/ethyl acetate (5:1 (v/v)) by silica gel column chromatography, thus obtaining 27 mg of an oil represented by formula 1-1 (yield: 39%; 4 step overall yield from resin 2-1; loading capacity of resin 2-1=0.90 mmol/g).

compound 1-1: $^1$H NMR (500 MHz, CDCl$_3$) δ 1.31 (s, 9H), 1.66 (s, 6H), 3.55 (s, 4H), 3.68 (m, 4H), 3.71 (m, 4H), 11.13 (s, 1H); m/z ([M+1]$^+$) 381.

Examples 1-2 to 1-60

Synthesis of 2,4-disubstituted-5-aminocarbonyl-1,3-thiazole derivatives 2,4-disubstituted-5-aminocarbonyl-1,3-thiazole derivatives were synthesized in the same manner as in Example 1, except that R$^1$, R$^2$, R$^3$ and R$^4$ in the compounds represented by formula 1 were as shown in Table 1 below. Also, the analysis results of the synthesized 2,4-disubstituted-5-aminocarbonyl-1,3-thiazole derivatives are shown in Table 1.

TABLE 1

[Formula 1]

| No. | R$^1$ R$^2$ | R$^3$ | R$^4$ | Analysis data [$^1$H NMR(500 MHz, CDCl$_3$) & Mass] |
|---|---|---|---|---|
| 1-1 | —CH$_2$CH$_2$OCH$_2$CH$_2$— | pivaloyl (C(=O)C(CH$_3$)$_3$) | piperidin-1-yl | $^1$H NMR δ 1.31(s, 9H), 1.66(s, 6H), 3.55(s, 4H), 3.68(m, 4H), 3.71(m, 4H), 11.13(s, 1H); m/z([M + 1]$^+$) 381 |
| 1-2 | —CH$_2$CH$_2$OCH$_2$CH$_2$— | pivaloyl (C(=O)C(CH$_3$)$_3$) | morpholin-4-yl | $^1$H NMR δ 1.30(s, 9H), 3.56(t, J=4.9 Hz, 4H), 3.66-3.68(m, 4H), 3.70-3.72(m, 4H), 3.77(d, J=5.0 Hz, 4H), 11.00(s, 1H); m/z ([M + 1]$^+$) 383 |
| 1-3 | —CH$_2$CH$_2$OCH$_2$CH$_2$— | pivaloyl (C(=O)C(CH$_3$)$_3$) | —NEt$_2$ | $^1$H NMR δ 1.27(m, 6H), 1.31(s, 9H), 3.56(m, 4H), 3.71-3.78(m, 8H), 11.08(s, 1H); m/z ([M + 1]$^+$) 369 |

TABLE 1-continued

[Formula 1]

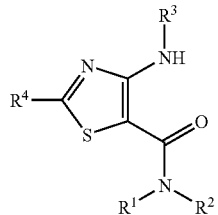

| No. | R¹ | R² | R³ | R⁴ | Analysis data [¹H NMR(500 MHz, CDCl₃) & Mass] |
|---|---|---|---|---|---|
| 1-4 | —CH₂CH₂OCH₂CH₂— | | tert-butyl C(=O) | 4-methylpiperazin-1-yl | ¹H NMR δ 1.27(s, 9H), 2.35(s, 3H), 2.54(t, J=5.1 Hz, 4H), 3.65(m, 4H), 3.69-3.74(m, 8H), 11.09(s, 1H); m/z([M + 1]⁺) 396 |
| 1-5 | —CH₂CH₂OCH₂CH₂— | | tert-butyl C(=O) | 4-phenylpiperazin-1-yl | ¹H NMR δ 1.29(s, 9H), 3.28(m, 4H), 3.65(m, 4H), 3.70(m, 4H), 3.83(s, 4H), 6.92-6.95(m, 3H), 7.45-7.48(m, 2H), 11.10(s, 1H); m/z ([M + 1]⁺) 458 |
| 1-6 | —CH₂CH₂OCH₂CH₂— | | tert-butyl C(=O) | 4-(3-methoxyphenyl)piperazin-1-yl | ¹H NMR δ 1.30(s, 9H), 3.28(t, J=5.2 Hz, 4H), 3.65(m, 4H), 3.70(m, 4H), 3.80(s, 3H), 3.86(br s, 4H), 6.47-6.50(m, 2H), 6.55(dd, J=1.8, 8.1 Hz, 1H), 7.20(t, J=8.1 Hz, 1H), 11.03(s, 1H); m/z([M + 1]⁺) 488 |
| 1-7 | —CH₂CH₂OCH₂CH₂— | | tert-butyl C(=O) | 4-(2-methoxyphenyl)piperazin-1-yl | ¹H NMR δ 1.32(s, 9H), 3.15(t, J=5.0 Hz, 4H), 3.70-3.73(m, 8H), 3.78(t, J=4.8 Hz, 4H), 3.88(s, 3H), 6.89-6.94(m, 3H), 7.05(m, 1H), 11.05(s, 1H); m/z([M + 1]⁺) 488 |
| 1-8 | —CH₂CH₂OCH₂CH₂— | | tert-butyl C(=O) | 4-(4-chlorophenyl)piperazin-1-yl | ¹H NMR δ 1.31(s, 9H), 3.24(t, J=5.2 Hz, 4H), 3.66(m, 4H), 3.71(m, 4H), 3.83(br s, 4H), 6.86(d, J=9.0 Hz, 2H), 7.24(d, J=9.0 Hz, 2H), 11.09(s, 1H); m/z([M + 1]⁺) 492 |
| 1-9 | —CH₂CH₂OCH₂CH₂— | | tert-butyl C(=O) | 4-(2-chlorophenyl)piperazin-1-yl | ¹H NMR δ 1.30(s, 9H), 3.15(t, J=5.0 Hz, 4H), 3.64(m, 4H), 3.72(m, 4H), 3.87(br s, 4H), 7.01-7.05(m, 2H), 7.24(m, 1H), 7.39(dd, J=1.3, 7.8 Hz, 1H), 11.11(s, 1H); m/z ([M + 1]⁺) 492 |
| 1-10 | —CH₂CH₂OCH₂CH₂— | | tert-butyl C(=O) | benzylamino | ¹H NMR δ 1.26(s, 9H), 3.65(m, 4H), 3.70(m, 4H), 4.45(s, 2H), 7.26-7.31(m, 5H), 11.13 (s, 1H); m/z([M + 1]⁺) 403 |
| 1-11 | —CH₂CH₂OCH₂CH₂— | | tert-butyl C(=O) | 4-methoxybenzylamino | ¹H NMR δ 1.28(s, 9H), 3.66(m, 4H), 3.72(m, 7H), 4.36(s, 2H), 6.76(m, 2H), 7.45(m, 2H), 11.10(s, 1H); m/z([M + 1]⁺) 433 |
| 1-12 | —CH₂CH₂OCH₂CH₂— | | tert-butyl C(=O) | 2-(piperidin-1-yl)ethylamino | ¹H NMR δ 1.31(s, 9H), 1.66(m, 2H), 1.94(m, 4H), 3.22(m, 4H), 3.43(m, 2H), 3.69(m, 8H), 3.84(m, 2H), 11.40(s, 1H); m/z([M + 1]⁺) 424 |

TABLE 1-continued

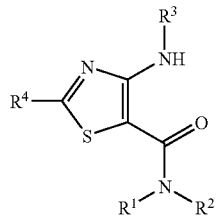

[Formula 1]

| No. | R¹ | R² | R³ | R⁴ | Analysis data [$^1$H NMR(500 MHz, CDCl$_3$) & Mass] |
|---|---|---|---|---|---|
| 1-13 | —CH$_2$CH$_2$OCH$_2$CH$_2$— | | pivaloyl | 2-(pyrrolidin-1-yl)ethylamino | $^1$H NMR δ 1.30(s, 9H), 1.39-1.72(m, 2H), 1.97-2.03(m, 2H), 2.71(m, 4H), 3.21-3.26(m, 2H), 3.43(m, 2H), 3.66-3.72(m, 8H), 11.31 (s, 1H); m/z([M + 1]$^+$) 410 |
| 1-14 | —CH$_2$CH$_2$OCH$_2$CH$_2$— | | pivaloyl | 4-morpholinopiperidin-1-yl | $^1$H NMR δ 1.30(s, 9H), 1.60(m, 2H), 1.93(m, 2H), 2.47(m, 1H), 2.57(t, J=4.5 Hz, 4H), 3.09(m, 2H), 3.66-3.68(m, 4H), 3.70-3.73(m, 8H), 4.12(m, 2H), 11.07(s, 1H); m/z([M + 1]$^+$) 466 |
| 1-15 | —CH$_2$CH$_2$OCH$_2$CH$_2$— | | pivaloyl | 4-(pyrrolidin-1-yl)piperidin-1-yl | $^1$H NMR δ 1.29(s, 9H), 1.90(m, 2H), 1.99(s, 4H), 2.12(d, J=11.8 Hz, 2H), 2.89(m, 1H), 3.03(s, 4H), 3.10(dt, J=2.6, 13.3 Hz, 2H), 3.65-3.67(m, 4H), 3.69-3.71(m, 4H), 4.15(d, J=13.3 Hz, 2H), 10.95(s, 1H); m/z([M + 1]$^+$) 450 |
| 1-16 | —CH$_2$CH$_2$OCH$_2$CH$_2$— | | pivaloyl | 4-(piperidin-1-yl)piperidin-1-yl | $^1$H NMR δ 1.31(s, 9H), 1.52(m, 2H), 1.69(m, 2H), 1.76(br s, 4H), 2.06(d, J=11.5 Hz, 2H), 2.69(br s, 4H), 2.78(m, 1H), 3.07(m, 2H), 3.69(m, 4H), 3.73(m, 2H), 4.19(d, J= 13.0 Hz, 2H), 11.06(s, 1H); m/z([M + 1]$^+$) 464 |
| 1-17 | —CH$_2$CH$_2$OCH$_2$CH$_2$— | | valeryl | piperidin-1-yl | $^1$H NMR δ 0.91(t, J=7.4 Hz, 3H), 1.38(m, 2H), 1.66(s, 6H), 1.68(m, 2H), 2.46(m, 2H), 3.51(s, 4H), 3.65-3.67(m, 4H), 3.69-3.71(m, 4H), 10.40(s, 1H); m/z([M + 1]$^+$) 381 |
| 1-18 | —CH$_2$CH$_2$OCH$_2$CH$_2$— | | valeryl | morpholino | $^1$H NMR δ 0.91(t, J=7.4 Hz, 3H), 1.38(m, 2H), 1.67(m, 2H), 2.44(t, J=7.4 Hz, 2H), 3.53(t, J=4.9 Hz, 4H), 3.66(dd, J=3.5, 5.6 Hz, 4H), 3.70(dd, J=3.4, 5.4 Hz, 4H), 3.77(t, J=5.0 Hz, 4H), 10.28(s, 1H); m/z ([M + 1]$^+$) 383 |
| 1-19 | —CH$_2$CH$_2$OCH$_2$CH$_2$— | | valeryl | benzylamino | $^1$H NMR δ 0.88(t, J=7.4 Hz, 3H), 1.33(tq, J=7.5, 7.4 Hz, 2H), 1.62(m, 2H), 2.33(t, J= 7.2 Hz, 2H), 3.63(m, 4H), 3.68(m, 4H), 4.42(s, 2H), 7.27-7.31(m, 5H), 7.55(br s, 1H), 10.59(s, 1H); m/z([M + 1]$^+$) 403 |
| 1-20 | —CH$_2$CH$_2$OCH$_2$CH$_2$— | | valeryl | 2-(piperidin-1-yl)ethylamino | $^1$H NMR δ 0.89(t, J=7.4 Hz, 3H), 1.35(m, 2H), 1.59-1.66(m, 4H), 1.84(t, J=5.3 Hz, 4H), 2.36(t, J=7.6 Hz, 2H), 2.97-3.10(m, 4H), 3.24(s, 2H), 3.62-3.66(m, 10H), 8.65 (br s, 1H), 10.88(s, 1H); m/z([M + 1]$^+$) 424 |
| 1-21 | —CH$_2$CH$_2$OCH$_2$CH$_2$— | | valeryl | 4-morpholinopiperidin-1-yl | $^1$H NMR δ 0.91(t, J=7.4 Hz, 3H), 1.38(m, 2H), 1.59(m, 2H), 1.68(m, 2H), 1.93(dd, J= 1.7, 11.9 Hz, 2H), 2.43-2.47(m, 3H), 2.55(t, J=4.4 Hz, 4H), 3.09(m, 2H), 3.65-3.67(m, 4H), 3.68-3.72(m, 8H), 4.07(d, J=13.1 Hz, 2H), 10.36(s, 1H); m/z([M + 1]$^+$) 466 |

TABLE 1-continued

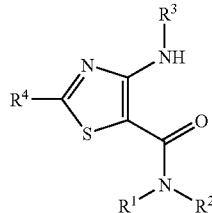

[Formula 1]

| No. | R¹ | R² | R³ | R⁴ | Analysis data [¹H NMR(500 MHz, CDCl₃) & Mass] |
|---|---|---|---|---|---|
| 1-22 | —CH₂CH₂OCH₂CH₂— | | (ketone-butyl-pyrrolidine) | (piperidine) | ¹H NMR δ 0.88(t, J=7.4 Hz, 3H), 1.36(m, 2H), 1.63(m, 2H), 2.03-2.09(m, 5H), 2.21(d, J=11.7 Hz, 2H), 2.41(t, J=7.4 Hz, 2H), 2.95-3.00(m, 8H), 3.60-3.62(m, 4H), 3.66-3.68(m, 4H), 4.12(d, J=13.2 Hz, 2H), 10.14(s, 1H); m/z([M + 1]⁺) 450 |
| 1-23 | —CH₂CH₂OCH₂CH₂— | | —C(O)CH₃ | (2-methoxyphenyl-piperazine) | ¹H NMR δ 2.37(s, 3H), 3.16(m, 4H), 3.69-3.74(m, 8H), 3.78(t, J=5.1 Hz, 4H), 3.85(s, 3H), 6.89-6.93(m, 3H), 7.05(m, 1H), 10.82(s, 1H); m/z([M + 1]⁺) 446 |
| 1-24 | —CH₂CH₂OCH₂CH₂— | | (cyclohexyl ketone) | (2-methoxyphenyl-piperazine) | ¹H NMR δ 1.25-1.35(m, 3H), 1.58-1.61(m, 3H), 1.83-1.85(m, 2H), 2.06-2.09(m, 2H), 2.49(m, 1H), 3.15-3.17(m, 4H), 3.70-3.73(m, 8H), 3.81(m, 7H), 6.89-6.93(m, 3H), 7.05(m, 1H), 11.05(s, 1H); m/z([M + 1]⁺) 514 |
| 1-25 | —CH₂CH₂OCH₂CH₂— | | (cyclopropyl ketone) | (2-methoxyphenyl-piperazine) | ¹H NMR δ 0.93(m, 2H), 1.18(m, 2H), 1.86(m, 1H), 3.15(t, J=5.1 Hz, 4H), 3.69-3.75(m, 8H), 3.78(t, J=4.8 Hz, 4H), 3.89(s, 3H), 6.89-6.94(m, 3H), 7.05(m, 1H), 11.09(s, 1H); m/z([M + 1]⁺) 472 |
| 1-26 | —CH₂(CH₂)₃CH₂— | | (t-butyl ketone) | CH₃(CH₂)₂NH— | m/z([M + 1]⁺) 353 |
| 1-27 | —CH₂(CH₂)₃CH₂— | | (t-butyl ketone) | (cyclopropylmethylamino) | ¹H NMR δ 0.25(m, 2H), 0.56(m, 2H), 1.10(m, 1H), 1.26(s, 9H), 1.60(m, 4H), 1.66(m, 2H), 3.11(d, J=6.8 Hz, 2H), 3.57(t, J=5.0 Hz, 4H), 11.16(s, 1H); m/z([M + 1]⁺) 365 |
| 1-28 | —CH₂(CH₂)₃CH₂— | | (t-butyl ketone) | (cyclohexylmethylamino) | m/z([M + 1]⁺) 407 |
| 1-29 | —CH₂(CH₂)₃CH₂— | | (t-butyl ketone) | (benzylamino) | ¹H NMR δ 1.26(s, 9H), 1.59(m, 4H), 1.66(m, 2H), 3.58(t, J=5.1 Hz, 4H), 4.44(s, 2H), 7.27-7.29(m, 5H), 11.18(s, 1H); m/z([M + 1]⁺) 401 |
| 1-30 | —CH₂(CH₂)₃CH₂— | | (t-butyl ketone) | (piperidinyl-ethylamino) | ¹H NMR δ 1.30(s. 9H), 1.58-1.61(m, 4H), 1.65-1.67(m, 4H), 1.90(t, J=5.0 Hz, 4H), 3.11-3.15(m, 4H), 3.34(m, 2H), 3.61(t, J= 5.4 Hz, 4H), 3.77(m, 2H), 11.43(s, 1H); m/z ([M + 1]⁺) 422 |

TABLE 1-continued

[Formula 1]

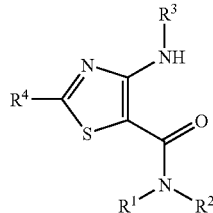

| No. | R¹ | R² | R³ | R⁴ | Analysis data [¹H NMR(500 MHz, CDCl₃) & Mass] |
|---|---|---|---|---|---|
| 1-31 | —CH₂(CH₂)₃CH₂— | | (pivaloyl group) | 2-methoxyphenyl-piperazinyl | ¹H NMR δ 1.32(s, 9H), 1.62(m, 4H), 1.67(m, 2H), 3.15(t, J=4.9 Hz, 4H), 3.63(t, J= 5.2 Hz, 4H), 3.78(t, J=4.8 Hz, 4H), 3.88 (s, 3H), 6.89-6.94(m, 3H), 7.04(m, 1H), 11.17(s, 1H); m/z([M + 1]⁺) 486 |
| 1-32 | —CH₂(CH₂)₃CH₂— | | (pivaloyl group) | 2-methylphenyl-piperazinyl | ¹H NMR δ 1.31(s, 9H), 1.63(m, 4H), 1.67(m, 2H), 2.33(s, 3H), 3.01(t, J=5.0 Hz, 4H), 3.63(m, 4H), 3.83(m, 4H), 6.99(d, J=7.9 Hz, 1H), 7.03(m, 1H), 11.21(s, 1H);; m/z ([M + 1]⁺) 470 |
| 1-33 | —CH₂(CH₂)₃CH₂— | | (pivaloyl group) | 2-fluorophenyl-piperazinyl | ¹H NMR δ 1.31(s, 9H), 1.61(m, 4H), 1.67(m, 2H), 3.17(t, J=5.0 Hz, 4H), 3.64(t, J= 5.1 Hz, 4H), 3.81(m, 4H), 6.94(m, 1H), 7.00 (m, 1H), 7.04-7.08(m, 2H), 11.19(s, 1H); m/z ([M + 1]⁺) 474 |
| 1-34 | —CH₂(CH₂)₃CH₂— | | (pivaloyl group) | 4-fluorophenyl-piperazinyl | ¹H NMR δ; m/z([M + 1]⁺) 474 |
| 1-35 | —CH₂(CH₂)₃CH₂— | | (pivaloyl group) | 2-cyanophenyl-piperazinyl | ¹H NMR δ; m/z([M + 1]⁺) 481 |
| 1-36 | —CH₂(CH₂)₃CH₂— | | (pivaloyl group) | 2-pyridyl-piperazinyl | ¹H NMR δ; m/z([M + 1]⁺) 457 |
| 1-37 | —CH₂(CH₂)₃CH₂— | | (pivaloyl group) | 4-morpholinopiperidinyl | ¹H NMR δ 1.30(s, 9H), 1.57-1.63(m, 6H), 1.65(m, 2H), 1.95(d, J=12.7 Hz, 2H), 2.52 (tt, J=3.3, 11.2 Hz, 1H), 2.61(t, J=4.4 Hz, 4H), 3.08(dt, J=2.3, 12.6 Hz, 2H), 3.60 (t, J=5.4 Hz, 4H), 3.74(t, J=4.6 Hz, 4H), 4.13(d, J=13.1 Hz, 2H), 11.16(s, 1H); m/z ([M + 1]⁺) 464 |
| 1-38 | —CH₂(CH₂)₃CH₂— | | (pivaloyl group) | 4-piperidinopiperidinyl | ¹H NMR δ 1.31(s, 9H), 1.51(m, 2H), 1.59-1.76(m, 12H), 2.05(br s, 2H), 2.68(br s, 5H), 3.07(dt, J=2.2, 12.7 Hz, 2H), 3.62 (t, J=5.4 Hz, 4H), 4.20(d, J=12.9 Hz, 2H), 11.18(s, 1H); m/z([M + 1]⁺) 462 |
| 1-39 | —CH₂(CH₂)₃CH₂— | | (butanoyl group) | piperidinyl | ¹H NMR δ 0.91(t, J=7.4 Hz, 3H), 1.37(tq, J=7.4, 7.4 Hz, 2H), 1.57-1.61(m, 4H), 1.65 (s, 8H), 1.68(m, 2H), 2.46(m, 2H), 3.51(s, 4H), 3.59(t, J=5.4 Hz, 4H), 10.52(s, 1H); m/z([M + 1]⁺) 379 |

TABLE 1-continued

[Formula 1]

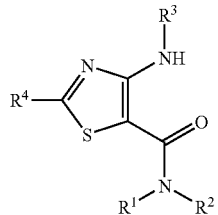

| No. | R¹ | R² | R³ | R⁴ | Analysis data [$^1$H NMR(500 MHz, CDCl$_3$) & Mass] |
|---|---|---|---|---|---|
| 1-40 | —CH$_2$(CH$_2$)$_3$CH$_2$— | | (ketone-propyl-morpholine) | | $^1$H NMR δ 0.91(t, J=7.4 Hz, 3H), 1.38(tq, J=7.5, 7.4 Hz, 2H), 1.58-1.62(m, 4H), 1.65-1.71(m, 4H), 2.44(t, J=7.1 Hz, 2H), 3.54(t, J=4.9 Hz, 4H), 3.60(t, J=5.5 Hz, 4H), 3.78(t, J=4.9 Hz, 4H), 10.43(s, 1H); m/z([M + 1]$^+$) 381 |
| 1-41 | —CH$_2$(CH$_2$)$_3$CH$_2$— | | (ketone-propyl-benzylamino) | | $^1$H NMR δ 0.89(t, J=7.4 Hz, 3H), 1.35(tq, J=7.5, 7.4 Hz, 2H), 1.56-1.68(m, 8H), 2.35 (t, J=7.6 Hz, 2H), 3.57(t, J=5.4 Hz, 4H), 4.42(s, 2H), 7.00(br s, 1H), 7.25-7.33(m, 5H), 10.65(s, 1H); m/z([M + 1]$^+$) 401 |
| 1-42 | —CH$_2$(CH$_2$)$_3$CH$_2$— | | (ketone-propyl-piperidinyl-ethyl-amino) | | $^1$H NMR δ 0.89(t, J=7.4 Hz, 3H), 1.34(tq, J=7.3, 7.4 Hz, 2H), 1.53-1.66(m, 10H), 1.83-1.88(m, 4H), 2.36(t, J=7.6 Hz, 2H), 2.95-3.10(m, 4H), 3.23(s, 2H), 3.56(t, J=5.4 Hz, 4H), 3.68(s, 2H), 8.57(br s, 1H), 10.97(s, 1H); m/z([M + 1]$^+$) 422 |
| 1-43 | —CH$_2$(CH$_2$)$_3$CH$_2$— | | (ketone-propyl-morpholinyl-piperidinyl) | | $^1$H NMR δ 0.91(t, J=7.3 Hz, 3H), 1.38(tq, J=7.5, 7.4 Hz, 2H), 1.56-1.72(m, 10H), 1.94 (d, J=11.4 Hz, 2H), 2.44-2.49(m, 3H), 2.57 (t, J=4.5 Hz, 4H), 3.08(dt, J=2.8, 13.1 Hz, 2H), 3.59(t, J=5.4 Hz, 4H), 3.73(t, J=4.5 Hz, 4H), 4.09(d, J=13.2 Hz, 2H), 10.49(s, 1H); m/z([M + 1]$^+$) 464 |
| 1-44 | —CH$_2$(CH$_2$)$_3$CH$_2$— | | (ketone-propyl-pyrrolidinyl-piperidinyl) | | $^1$H NMR δ 0.91(t, J=7.4 Hz, 3H), 1.37(tq, J=7.4, 7.4 Hz, 2H), 1.58-1.62(m, 4H), 1.65-1.71(m, 4H), 1.91(m, 2H), 2.02(m, 3H), 2.14(d, J=11.9 Hz, 2H), 2.43(t, J=7.2 Hz, 2H), 2.85(m, 2H), 3.03(m, 2H), 3.09(dt, J=2.4, 13.3 Hz, 2H), 3.59(t, J=5.4 Hz, 4H), 4.13(d, J=13.3 Hz, 2H), 10.40(s, 1H); m/z([M + 1]$^+$) 448 |
| 1-45 | —CH$_2$(CH$_2$)$_2$CH$_2$— | | (t-butyl ketone-benzylamino) | | $^1$H NMR δ 1.28(s, 9H), 1.93(m, 4H), 3.61(m, 4H), 4.44(s, 2H), 7.27-7.30(m, 5H), 11.89 (s, 1H); m/z([M + 1]$^+$) 387 |
| 1-46 | —CH$_2$(CH$_2$)$_2$CH$_2$— | | (t-butyl ketone-piperidinyl-ethyl-amino) | | $^1$H NMR δ 1.31(s, 9H), 1.69(m, 2H), 1.93-1.97(m, 8H), 3.30(br s, 4H), 3.53(t, J=4.7 Hz, 2H), 3.61(m, 4H), 3.89(m, 2H), 12.12(s, 1H); m/z([M + 1]$^+$) 408 |
| 1-47 | —CH$_2$(CH$_2$)$_2$CH$_2$— | | (t-butyl ketone-morpholinyl-ethyl-amino) | | m/z([M + 1]$^+$) 410 |

TABLE 1-continued

[Formula 1]

| No. | R¹ | R² | R³ | R⁴ | Analysis data [¹H NMR(500 MHz, CDCl₃) & Mass] |
|---|---|---|---|---|---|
| 1-48 | —CH₂(CH₂)₂CH₂— | | pivaloyl (C(=O)C(CH₃)₃) | 3-(morpholin-4-yl)propylamino | m/z([M + 1]⁺) 424 |
| 1-49 | —CH₂(CH₂)₂CH₂— | | pivaloyl | 4-(2-methoxyphenyl)piperazin-1-yl | ¹H NMR δ 1.34(s, 9H), 1.96(m, 4H), 3.16(t, J=5.0 Hz, 4H), 3.66(t, J=6.4 Hz, 4H), 3.79(t, J=4.6 Hz, 4H), 3.88(s, 3H), 6.89-6.94(m, 3H), 7.04(m, 1H), 11.97(s, 1H); m/z([M + 1]⁺) 472 |
| 1-50 | —CH₂(CH₂)₂CH₂— | | pivaloyl | (pyridin-4-ylmethyl)amino | m/z([M + 1]⁺) 381 |
| 1-51 | —CH₂(CH₂)₂CH₂— | | pivaloyl | (naphthalen-2-ylmethyl)amino | m/z([M + 1]⁺) 388 |

Test Example 1

Control of Cellular Division and Proliferation

Treatment of cells with sphingosylphosphorylcholine (SPC) can induce excessive cellular division and proliferation, thus causing pathological skin conditions [Desai, *Biochem. Biophys. Res. Commun.*, 1991, 181, 361-366]. Accordingly, the compounds prepared in the above Examples were tested for an effect on cellular division and proliferation induced by SPC.

First, $1\times10^5$ (usually $1\times10^4 \sim 10^5$) NIH 3T3 cells (American Type Culture Collection, Manassas, Va., USA) were dispensed and cultured on a culture plate, and then cultured in RPMI medium containing no fetal bovine serum for 24 hours to achieve serum starvation. The cells were treated with the compounds prepared in the above Examples, and FTY720, a sphingosine-1-phosphate (S1P) agonist, at concentrations of 0.001 μM, 0.01 μM, 0.1 μM and 1 μM, and were incubated for 30 minutes. Then, SPC (Biomol, Plymouth Meeting, Pa., USA) was added thereto at a concentration of 7 μM, and the cells were incubated at 37° C. for 24 hours. The amount of cell proliferation was assayed by [3H]-thimidine incorporation into DNA strands replicated during cell division [Beales I L, *Life Sci.*, 2004, 75, 83-95]. Cell proliferation (%) was calculated according to the following equation 1, and the results are shown in Table 1.

Proliferation %=(group treated with test drug−group not treated with SPC)/(group treated with SPC alone−group not treated with SPC)×100    [Equation 1]

TABLE 2

| Example | antagonistic effect on SPC IC₅₀ (μM) |
|---|---|
| 1-1 | 0.932 |
| 1-2 | — |
| 1-3 | — |
| 1-4 | — |
| 1-5 | 0.189 |
| 1-6 | — |
| 1-7 | 0.271 |
| 1-8 | 0.73 |
| 1-9 | 0.86 |
| 1-10 | 0.068 |
| 1-11 | 0.0937 |
| 1-12 | 0.00581 |
| 1-13 | 0.0127 |
| 1-14 | 0.0093 |
| 1-15 | 0.0207 |
| 1-16 | 0.103 |
| 1-17 | — |
| 1-18 | — |
| 1-19 | 0.079 |
| 1-20 | 0.0075 |

TABLE 2-continued

| Example | antagonistic effect on SPC IC$_{50}$ (μM) |
|---|---|
| 1-21 | 0.057 |
| 1-22 | 0.096 |
| 1-23 | 0.85 |
| 1-24 | 0.91 |
| 1-25 | 0.067 |
| 1-26 | — |
| 1-27 | 0.308 |
| 1-28 | 0.716 |
| 1-29 | 0.00612 |
| 1-30 | 0.878 |
| 1-31 | 0.00542 |
| 1-32 | 0.045 |
| 1-33 | 0.0109 |
| 1-34 | 0.057 |
| 1-35 | 0.094 |
| 1-36 | 0.54 |
| 1-37 | 0.089 |
| 1-38 | 0.176 |
| 1-39 | — |
| 1-40 | — |
| 1-41 | 0.0098 |
| 1-42 | 0.102 |
| 1-43 | — |
| 1-44 | 0.0883 |
| 1-45 | 0.97 |
| 1-46 | — |
| 1-47 | — |
| 1-48 | — |
| 1-49 | 0.178 |
| 1-50 | — |
| 1-51 | — |
| 1-52 | — |
| 1-53 | — |
| 1-54 | — |
| 1-55 | — |
| 1-56 | — |
| 1-57 | — |
| 1-58 | — |
| 1-59 | — |
| 1-60 | — |

As can be seen in Table 2 above, the compounds prepared in Examples of the present invention showed an antagonist effect on selective cell proliferation induced by SPC. Since excessive cellular division and proliferation caused by an inflammation reaction occurring in the process in which an external wound is healed leads to scar formation, substances of inhibiting cellular division and proliferation can be used to prevent unnecessary scar formation. In addition, the substances of inhibiting cellular division and proliferation can be used to promote post-traumatic wound healing.

Particularly, the compounds of Examples 1-12, 1-29 and 1-31 dose-dependently inhibited cellular division and proliferation induced by SPC. Noteworthily, the compounds having a structure similar to that of SPC, the S1P agonist FTY720 holding some membrane receptors did not inhibit cellular division and proliferation by SPC. Accordingly, cellular division and proliferation is induced by the inherent structural activity of the inventive compounds, and the inventive compounds can inhibit scar formation resulting from excessive cellular division and proliferation caused by an inflammatory reaction occurring in a wound healing process.

Test Example 2

Inhibitory Effect on Chemotactic Cell Migration Induced by SPC

Recently, it was reported that SPC plays an important role in chemotactic cell migration, similar to vascular endothelial cell growth (VEGF) [Boguslawski et al, *Biochem Biophys Res Commun.*, 2000, 272, 603-609]. The phenomenon in which cells migrate in a living body by special cytokines or kemokines is a key step in a process, such as migration of immune cells to sites of inflammation, or angiogenesis caused by endothelial cells. Accordingly, the effect of the compounds prepared in the above Examples on chemotactic cell migration induced by SPC was tested by Boyden chamber analysis.

First, a 25×80 mm polycarbonate membrane (Neuro Probe, Inc.) having 8 μm pores was overnight coated by immersion in a solution containing 0.01% gelatin and 0.1% acetic acid solution and was naturally dried at room temperature.

Meanwhile, human umbilical vein endothelial cells (HU-VECs) cultured in complete EBM-2 medium containing 2% fetal bovine serum were incubated in EBM-2 medium (Cambrex, Catalog No. CC-3121) containing no fetal bovine serum for 4 hours to achieve serum starvation, and then the cells were harvested with trypsin/EDTA solution. The HUVEC cells were suspended in EBM-2 medium containing 0.1% fetal bovine serum. Then, the cells were dispensed in a silicon-coated Eppendorf tube, the compound of Example 1-31 as a test drug was added to the cells in amounts of 0.1, 1 and 10 μg/ml, and the cells were treated with the compound at 37° C. for 30 minutes. 27 μL of EBM-2 medium containing 10 μM SPC or EBM-2 medium containing no SPC was dispensed in each well of the lower chamber of the Boyden chamber, and a gelatin-coated membrane was placed in the lower chamber, such that the glossy surface of the membrane was faced downward. A gasket was placed on the membrane, and then the upper chamber was assembled. $5 \times 10^4$ (56 μl) HUVEC cells treated with the drug were dispensed in each well of the upper chamber and incubated in a $CO_2$ incubator at 37° C. for 8 hours. The membrane was separated, stained with Diff-Quik dye (Sysmex Corporation), washed with deionized water, and then attached to a slide glass, such that the glossy surface was faced downward. The cells attached onto the membrane were carefully wiped with kimwipes or cotton swabs, and then each well was photographed in five fields (200× magnification), and the cells were counted. Inhibition of chemotactic cell migration was calculated according to the following equation 2, and the results are shown in Table 3 below.

Inhibition %=(group treated with SPC alone–group treated with test drug)/(group treated with SPC alone–group not treated with SPC)×100     [Equation 2]

TABLE 3

| Example | Inhibition (%) | | |
|---|---|---|---|
| | 0.1 μg/ml | 1 μg/ml | 10 μg/ml |
| 1-31 | 44 | 58 | 69 |

As can be seen in Table 3 above, the compound of Example 1-31 of the present invention strongly inhibited chemotactic cell migration caused by SPC. This suggests that the compound of the present invention can inhibit endothelial cell or immune cell migration in vivo to control processes, such as angiogenesis in tumors, and amplification of immune responses to external antigens.

Test Example 3

Control of Inflammatory Reaction in Mouse TPA-Induced Inflammation Model

In order to examine an inhibitory effect on inflammatory reactions, the following test was carried out using tetradecanoyl phorbol acetate (hereinafter referred to as "TPA")-induced inflammation model.

The TPA-induced inflammation model was a test method which has been widely used to test inflammatory reaction mechanisms and the effect of inhibitory substances [De Young L M et al., *Agents and Actions,* 1989, 26, 335-341]. When TPA which is a substance causing an inflammatory reaction is applied to the ear of a test subject, erythema and edema occur. Such inflammatory reactions are measurable through the increase in the activity of myeloperoxidase (MPO) which is essential for bacterial invasion into white blood cells.

Forty 6-week-old ICR mice were prepared, and 20 μl of a TPA solution (Sigma Aldrich Korea) obtained by dissolving TPA in acetone at a concentration of 125 μg/ml was applied to the left ear of each animal. At 1 hour after the application of TPA, 20 μl of each of acetone, the compounds of Examples dissolved in acetone at a concentration of 0.3%, and hydrocortisone (Sigma Aldrich Korea) dissolved in acetone at a concentration of 0.3% was applied to the TPA-applied site, and at 6 hours after the application of TPA, it was applied again to the same site in the same amount (20 μl). At 24 hours after the application of TPA, the mice were sacrificed by cervical dislocation, and the left ear was collected in a given width and measured for weight and MPO activity. Inhibition % of inflammatory reactions was calculated according to the following equation 3, and the results are shown in Table 4 below.

Inhibition %=(group treated with TPA alone−group treated with test drug)/(group treated with TPA alone−group not treated with TPA)×100     [Equation 3]

TABLE 4

| Examples (0.3%) | Inhibition (%) (MPO inhibition) |
| --- | --- |
| 1-1 | 21 |
| 1-5 | 30 |
| 1-10 | 68 |
| 1-11 | 49 |
| 1-12 | 86 (80) |
| 1-14 | 71 |
| 1-20 | 62 |
| 1-21 | 52 |
| 1-22 | 53 (48) |
| 1-28 | 43 |
| 1-29 | 87 (83) |
| 1-30 | 59 |
| 1-31 | 84 (78) |
| 1-32 | 43 |
| 1-33 | 47 |
| 1-37 | 44 (47) |
| 1-41 | 51 |
| 1-44 | 57 |
| 1-49 | 38 |
| Hydrocortisone | 85 |

As can be seen in Table 4 above, the compounds of Examples 1-12, 1-29 and 1-31 significantly inhibited TPA-induced inflammatory reactions in terms of two measures, ear edema and MPO activity, and the magnitude of the effects thereof was equal to that of hydrocortisone which is widely used as an anti-inflammatory drug. The above results suggest that the skin anti-inflammatory effect of the compounds of Examples 1-12, 1-29 and 1-31 inhibited neutrophil invasion into sites of inflammation.

Formulation Example 1

Preparation of Tablet (Compressing Method)

5.0 mg of the compound represented by formula 1 as an active ingredient was sieved, and then mixed with 14.1 mg of lactose, 0.8 mg of Crospovidone USNF and 0.1 mg of magnesium stearate. The mixture was compressed into a tablet.

Formulation Example 2

Preparation of Tablet (Wet Granulation)

5.0 mg of the compound represented by formula 1 as an active ingredient was sieved, and then mixed with 16.0 mg of lactose and 4.0 mg of starch. 0.3 mg of polysorbate 80 was dissolved in pure water, and then added to the mixture in a suitable amount, and the mixture was granulated. After drying, the granules were sieved, and then mixed with 2.7 mg of colloidal silicon oxide and 2.0 mg of magnesium stearate. The granules compressed into a tablet.

Formulation Example 3

Preparation of Powder and Capsule 5.0 mg of the compound represented by formula 1 as an active ingredient was sieved, and then mixed with 14.8 mg of lactose, 10.0 mg of polyvinylpyrrolidone and 0.2 mg of magnesium stearate. The mixture was filled in No. 5 gelatin capsule using a suitable apparatus.

Formulation Example 4

Preparation of Injection Solution 100 mg of the compound represented by formula 1 as an active ingredient was mixed with 180 mg of mannitol, 26 mg of $Na_2HPO_4 \cdot 12H_2O$ and 2,974 mg of distilled water, thus preparing an injection solution.

As described above, the present invention provides 2,4-disubstituted-5-aminocarbonyl-1,3-thiazole derivatives or pharmaceutically acceptable salts thereof, which are prepared using a solid-phase combinatorial synthetic technique.

Furthermore, according to the present invention, the anti-inflammatory effect of the 2,4-disubstituted-5-aminocarbonyl-1,3-thiazole derivatives was analyzed through a test employing human dermal cells and an animal test using mice and, as a result, it was found that the compounds of the present invention showed excellent inhibitory activity on SPC receptor.

In addition, the present invention provides an SPC receptor inhibitor containing the 2,4-disubstituted-5-aminocarbonyl-1,3-thiazole derivative as an active ingredient, and furthermore, provides the use of the derivative as a therapeutic agent for treating inflammatory diseases induced by SPC receptor.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A 2,4-disubstituted-5-aminocarbonyl-1,3-thiazole compound represented by the following formula 1:

[Formula 1]

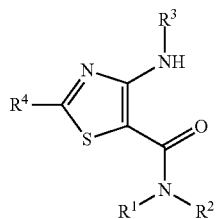

wherein

R$^1$ and R$^2$ are independently selected from the group consisting of a C$_1$-C$_{10}$ linear alkyl group, a C$_3$-C$_{10}$ branched alkyl group, and a C$_1$-C$_{10}$ linear alkyl group substituted with a C$_3$-C$_{10}$ cycloalkyl group, or R$^1$ and R$^2$ together with the nitrogen atom to which they are attached form a C$_3$-C$_{10}$ heterocyclic group containing one or more heteroatoms independently selected from N, S and O;

R$^3$ is a carbonyl group substituted with at least one group selected from the group consisting of a C$_1$-C$_{10}$ linear alkyl group, a C$_3$-C$_{10}$ branched alkyl group, a C$_3$-C$_{10}$ cyclic group, a C$_1$-C$_{10}$ alkoxy group, a C$_2$-C$_{10}$ alkenyl group, a C$_2$-C$_{10}$ alkynyl group, a heteroaryl group, an arylalkyl group, a C$_5$-C$_{10}$ heteroarylalkyl group, and a phenyl or substituted phenyl group; and R$^4$ is selected from the group consisting of piperidinyl, morpholino, 4-methoxybenzylamino, piperidin-1-ylethylamino, pyrrolidin-1-ylethylamino, 2-morpholinoethylamino, 2-morpholinopropylamino, 4-morpholinopiperidin-1-yl, 4-pyrrolidin-1-ylpiperidin-1-yl, 1,4'-bipiperidin-1'-yl, cyclopropylmethylamino, cyclohexylmethylamino, or R$^4$ is —NR$_a$R$_b$ wherein R$_a$ and R$_b$ are independently selected from the group consisting of a hydrogen, C$_1$-C$_{10}$ linear alkyl group, a C$_3$-C$_{10}$ branched alkyl group, a C$_3$-C$_{10}$ cyclic group, an aryl group, a heteroaryl group, an aryl(C$_1$-C$_{10}$)alkyl group a heteroaryl(C$_1$-C$_{10}$)alkyl group, or R$^4$ is a piperazinyl substituted with a group selected from the group consisting of C$_1$-C$_{10}$ linear alkyl group, a C$_3$-C$_{10}$ branched alkyl group, a C$_3$-C$_{10}$ cyclic group, a phenyl or substituted phenyl group, and a heteroaryl group, wherein the substituted phenyl group in R$^3$ and R$^4$ represents a phenyl group substituted with 1 to 4 substituents independently selected from the group consisting of a halogen atom, a cyano group, a C$_1$-C$_{10}$ alkyl group, and a C$_1$-C$_{10}$ alkoxy group, or a pharmaceutically acceptable salt thereof.

2. The 2,4-disubstituted-5-aminocarbonyl-1,3-thiazole compound of claim 1, wherein R$^1$ and R$^2$ are independently selected from the group consisting of a C$_1$-C$_5$ linear alkyl group and a C$_3$-C$_{10}$ branched alkyl group, or R$^1$ and R$^2$ together with the nitrogen atom to which they are attached form a C$_5$-C$_7$ heterocyclic group containing one or more heteroatoms independently selected from the group consisting of N, S and O;

R$^3$ is a carbonyl group substituted with at least one group selected from the group consisting of a C$_1$-C$_5$ linear alkyl group, a C$_3$-C$_5$ branched alkyl group, a C$_3$-C$_6$ cyclic alkyl group, a C$_2$-C$_5$ alkenyl group, a C$_2$-C$_5$ alkynyl group, a heteroaryl group, an arylalkyl group, a heteroaryl(C$_5$-C$_{10}$)alkyl group, and a phenyl or a substituted phenyl group; and R$^4$ is selected from the group consisting of piperidinyl, morpholino, 4-methoxybenzylamino, piperidin-1-ylethylamino, pyrrolidin-1-ylethylamino, 2-morpholinoethylamino, 2-morpholinopropylamino, 4-morpholinopiperidin-1-yl, 4-pyrrolidin-1-ylpiperidin-1-yl, 1,4'-bipiperidin-1'-yl, cyclopropylmethylamino, cyclohexylmethylamino, or R$^4$ is NR$_a$R$_b$ wherein R$_a$ and R$_b$ are independently selected from the group consisting of a hydrogen, C$_2$-C$_7$ linear alkyl group, a C$_3$-C$_7$ branched alkyl group, a C$_3$-C$_7$ cyclic group, an aryl group, a heteroaryl group, an aryl (C$_1$-C$_5$)alkyl group a heteroaryl(C$_1$-C$_5$)alkyl group, or R$^4$ is a piperazinyl substituted with a group selected from the group consisting of C$_1$-C$_7$ linear alkyl group, a C$_3$-C$_7$ branched alkyl group, a C$_3$-C$_7$ cyclic group, a phenyl or substituted phenyl group, and a heteroaryl group, wherein the substituted phenyl group in R$^3$ and R$^4$ represents a phenyl group substituted with 1 to 4 substituents independently selected from the group consisting of a halogen atom, a C$_1$-C$_5$ alkyl group, and a C$_1$-C$_5$ alkoxy group.

3. A method for treating atopic dermatitis induced by excessive cellular division and proliferation caused by sphingosylphosphorylcholine (SPC), which contains a compound of claim 1, wherein the compound has an antagonistic effect on selective cell proliferation induced by SPC.

4. The method of claim 3, wherein the compound is selected from the group consisting of N-{5-(morpholine-4-carbonyl)-2-[2-(piperidin-1-yl)ethylamino]thiazol-4-yl}pivalamide, N-[2-(benzylamino)-5-(piperidine-1-carbonyl)thiazol-4-yl]pivalamide, and N-{2-[4-(2-methoxyphenyl)-piperazin-1-yl]-5-(piperidine-1-carbonyl)thiazol-4-yl}pivalamide.

5. A skin external agent for inhibiting post-traumatic scar formation and promoting wound healing, the agent containing a compound of claim 1.

6. A method for inhibiting chemotactic cell migration caused by SPC in a cell comprising administering to the cell an effective amount of a compound of claim 1 to inhibit the chemotactic migration or a pharmaceutically acceptable salt thereof as an active ingredient.

7. The method of claim 6, wherein the compound is N-{2-[4-(2-methoxyphenyl)-piperazin-1-yl]-5-(piperidin-1-carbonyl)thiazol-4-yl}pivalamide.

* * * * *